US007361634B2

(12) United States Patent
Trotter et al.

(10) Patent No.: US 7,361,634 B2
(45) Date of Patent: Apr. 22, 2008

(54) PAIN-SENSITIVE THERAPEUTIC WOUND DRESSINGS

(75) Inventors: Patrick J. Trotter, Leeds (GB); Breda M. Cullen, Skipton (GB)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/554,375

(22) PCT Filed: Apr. 27, 2004

(86) PCT No.: PCT/GB2004/001774

§ 371 (c)(1),
(2), (4) Date: Oct. 25, 2005

(87) PCT Pub. No.: WO2004/096302

PCT Pub. Date: Nov. 11, 2004

(65) Prior Publication Data

US 2006/0286155 A1 Dec. 21, 2006

Related U.S. Application Data

(60) Provisional application No. 60/526,973, filed on Dec. 5, 2003.

(30) Foreign Application Priority Data

Apr. 28, 2003 (GB) ................................ 0309645.0

(51) Int. Cl.
*A61K 38/08* (2006.01)
*A61F 13/00* (2006.01)
*A61L 15/00* (2006.01)

(52) U.S. Cl. ............................. 514/2; 514/15; 514/16; 514/17; 424/445; 602/42; 602/48; 604/304

(58) Field of Classification Search ..................... None
See application file for complete search history.

(56) References Cited

U.S. PATENT DOCUMENTS 5,010,883 A * 4/1991 Rawlings et al. ............. 602/52
5,238,685 A * 8/1993 Wren ......................... 424/445
5,658,592 A * 8/1997 Tanihara et al. ............ 424/488
2005/0159695 A1* 7/2005 Cullen et al. ................. 602/48

FOREIGN PATENT DOCUMENTS

EP 0838224 A 4/1998
WO WO 00/64486 A 11/2000
WO WO 2004/030711 A 4/2004

OTHER PUBLICATIONS

Plendl J, Snyman C, Naidoo S, Sawant S, Mahabeer R and Bhoola KD, Expression of Tissue Kallikrein and Kinin Receptors in Angiogenic Microvascular Endotheial Cells, Biol. Chem., 2000, 381: 1103-1115.*

Ulbrich K, Stroham J, and Kopecek J, Polymers containing enzymatically degradable bonds V. Hydrophilic polymers degradable by chymotrysin, Biomaterials, 1982, 3: 150-154.*

Ulbrich K, Zacharieva El, Obereigner B and Kopecek J, Polymers containing enzymatically degradable bonds V. Hydrophilic polymers degradable by papain, Biomaterials, 1980, 1: 199-204.*

Chagas JR, Portaro FCV, Hirata IY, Almeida PC, Juliano M, Juliano L and Prado ES, Determinats of the unusual cleavage specificity of lysyl-bradykinin-releasing kallikreins, Biochem. J., 1995, 306: 63-69.*

Ulbrich, K. et al., "Polymers containing enzymically degradable bonds. V. Hydrophilic polymers degradable by papain", Biomaterials, 1(4) 199-204 (1980).

Del Nery, E. et al., "Comparison of human and porcine tissue kallikrein substrate specificities", Immunopharmacology, 45 (1-3), 151-157 (1999).

Suzuki, Y. et al., "A Novel Wound Dressing With An Antibiotic Delivery System Stimulated By Microbial Infection" Asaio Journal, vol. 43, No. 5 (1997).

Maeda, H. et al., "Kallikrein—kinin in infection and cancer", Immunopharmacology, 43 (2-3), 115-128 (1999).

International Search Report dated Aug. 18, 2004.

* cited by examiner

*Primary Examiner*—Anish Gupta
*Assistant Examiner*—Julie Ha

(57) ABSTRACT

The invention provides a wound dressing comprising a therapeutic agent and a matrix comprising polymers joined by cross-linkages which cross-linkages comprise oligopeptidic sequences which are cleavable by a kallikrein associated with wound fluid such that the rate of release of the therapeutic agent increases in the presence of elevated kallikrein levels.

10 Claims, No Drawings

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Arg Ser Ser Arg Gln
1               5


<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ile Ser Leu Met Lys Arg Pro Gln
1               5
```

PAIN-SENSITIVE THERAPEUTIC WOUND DRESSINGS

CROSS-REFERENCE TO RELATED APPLICATIONS

This application is a National Stage application under 35 U.S.C. 371 of PCT/GB2004/001774, filed 27 Apr. 2004, which claims priority from GB0309645.0 filed Apr. 28, 2003, and U.S. Provisional Application Ser. No. 60/526,973 filed Dec. 5, 2003.

The present invention relates to wound dressing materials, and in particular to new materials for the controlled release of therapeutic agents into wounds.

BACKGROUND

All publications, patents and patent applications cited herein are incorporated in full by reference.

In mammals, injury triggers an organised complex cascade of cellular and biochemical events that result in a healed wound. Wound healing is a complex dynamic process that results in the restoration of anatomic continuity and function; an ideally healed wound is one that has returned to normal anatomic structure, function and appearance.

Pain is associated with infected and chronic wounds. Biochemically, pain is experienced when there is an increase of kinins (bradykinin) in the area of the wound. Kinins are produced by the proteolytic breakdown of kininogen, and the protease responsible for this is kallikrein. Kallikrein also stimulates the production of tissue plasminogen activator (t-PA).

It is known to provide wound dressings containing therapeutic medicaments. For example, such dressings are known having a liquid permeable wound contacting layer, an intermediate absorbent layer and an outer, liquid-impervious backing layer, in which one or more of the layers contains a therapeutic agent. For example, EP-A-0599589 describes layered wound dressings having a wound contacting layer of a macromolecular hydrocolloid, an absorbent layer, and a continuous, microporous sheet intermediate the wound contacting layer and the absorbent layer. The absorbent layer contains a low molecular weight therapeutic agent that can diffuse into the wound.

WO-A-0238097 describes wound dressings comprising a liquid-permeable top sheet having a wound facing surface and a back surface, and a hydrogel layer on the wound-facing surface of the top sheet. The top sheet is adapted to block or restrict passage of liquid from the back surface to the wound-facing surface. The hydrogel layer is an insoluble hydrogel adapted to maintain a moist wound-healing environment at the wound surface. The hydrogel may contain therapeutic agents, such as antimicrobial agents, for sustained release into the wound.

Previous therapeutic wound dressings suffer from the drawback that the release of the therapeutic agent is relatively unresponsive to the condition of the wound being treated. This is undesirable because it can result in the development of resistance to the medication, and also because all unnecessary medication can interfere with the processes of wound healing.

SUMMARY

In one aspect, the present invention provides a wound dressing comprising a therapeutic agent and a matrix comprising polymers joined by cross-linkages which cross-linkages comprise oligopeptidic sequences which are cleavable by a kallikrein such that the rate of release of the therapeutic agent increases in the presence of the protease.

DETAILED DESCRIPTION

A first aspect of the invention provides a wound dressing comprising a therapeutic agent and a matrix comprising polymers joined by cross-linkages which cross-linkages comprise, or consist of, oligopeptidic sequences which are cleavable by a kallikrein such that the rate of release of the therapeutic agent increases in the presence of the protease.

Preferably, the matrix consists of the cross-linked polymers and optionally also the therapeutic agent.

By “a kallikrein” we include all serine proteases, whose activation, is associated with the degradation of kininogen to form kinins, which are implicated in the onset of pain. Serine proteases are a group of proteins which cut certain peptide bonds in other proteins. They all contain a serine at their active site (hence their name).

Examples include: Digestive enzymes such as trypsin and chymotrypsin; Clotting factors such as Factor X, Factor XI, Thrombin, and Plasmin; Proteins of the complement cascade such as C1r and C1s.

Proteases that have Kallikrein like activity include tissue kallikrein and plasma kallikrein. In addition, Kallikreins are also known as kinogenases or kininases.

They tend to be groups into two types, tissue and plasma kallikreins, each of which have many different isoforms. Kallikrein also exists as prekallikrein, which is cleaved by endogenous proteases into an active form. The half-life of kallikrein itself is very short in vivo (~15 s).

Plasma Kallikrein is encoded by 1 of 15 genes and therefore exists as one of many isoforms. It is manufactured in the liver and circulates as prekallikrein and binds to the surface of endothelial cells were it cleaves high molecular weight kininogen to liberate bradykinin. Plasma kallikreins in normal plasma are typically present in the range of 30-50 μg/ml. The level of kininogens in healthy plasma is typically 50-100 μg/ml Tissue Kallikrein differs in its origin (produced in many different tissues), molecular weight (27-40 kDa), substrate specificity and susceptibility to various inhibitors. Tissue kallikrein cleaves L and H-kininogens. There are therefore many types of tissue kallikrein which tend to be tissue specific but can be detected at low quantities in plasma.

Kallikreins are reviewed by Maeda, H. Wu, J., Okamoto, T., Maruo, K. and Akaike, T. in *Immunopharmacology* 43, 115-128 (1999), the entire content of which is incorporated herein by reference.

The levels of kallikreins and their precursors and reaction products are elevated in painful wounds and may also be elevated in wounds that are not painful but which go on to become painful within a few days. It is thought that the activity of the kallikreins in painful wound fluid is at least double, and in some cases at least four times that in normal healthy plasma.

The principle underlying the present invention is that the cross-linked polymers would behave as both an enzyme sensor and as an pain-dependent delivery system. In the absence of elevated levels of kallikreins the oligopeptidic sequences remain intact, keeping the pore size small and preventing (or at least keeping to low levels) the release of the therapeutic agent. Elevated pain protease levels (e.g. in wound infection or wound chronicity) hydrolyse the oligopeptidic sequences which results in increased pore size and permeability. The therapeutic agent is then released from the dressing so that it is free to migrate into the wound. In this way, delivery of the therapeutic agent increases in the presence of the protease so that if the wound is infected (including as indicated above when a protease associated with infection is elevated in a wound that is apparently not clinically infected but which goes on to become infected within a few days) or is a chronic wound delivery of the therapeutic agent increases.

By an "increase" in the rate of release of the therapeutic agent we include the situation where the rate of release of the therapeutic agent increases by at least 1.5, 2-, 3-, 4-, 5-, 6-, 7-, 8-, 9-, 10- or 15-fold in a painful wound relative to a non-painful wound. Typically, the rate of release of the therapeutic agent increases by at least 1.5, 2-, 3-, 4-, 5-, 6-, 7-, 8-, 9-, 10- or 15-fold in the presence of wound fluid containing kallikrein activity twice that of normal healthy serum. Preferably, there is no release of the therapeutic agent in the absence of the protease.

The term "polymer" as used herein includes homopolymers and copolymers (e.g. random copolymers, alternating copolymers and block copolymers).

Although polymers which are degraded by wound proteases could be used, it is preferred that the polymers are not degraded by the various proteases that may be present in the wound environment.

In theory, any polymer containing groups to which the reactive groups can be attached may be used, although of course the skilled person will appreciate that considerations such as toxicity should be taken into account. Similarly, the polymers used should not be immunogenic.

In selecting a polymer, charge and size may also be important as an increase in crystallinity will increase order and therefore reduce permeability of barrier. The longer the polymers the more likely they are to become physically intertwined, and consequently the less likely they are to fall apart. In view of this it is preferred that short polymers (i.e. 5 to 50 monomers) are used.

Preferably, a polyfunctional polymer is used as the pore size will be smaller and the ability to retain the therapeutic agent in the absence of protease will be higher.

Preferably, the polymers are non-ionic surfactants, polyalkoylated alcohols, alkyl or dialkyl polyglycerol compounds, polyethyloxylated alcohols, polymers (including homopolymers and copolymers) of acrylamide (e.g. N-(2-hydroxypropyl)methacrylamide (HPMA)), polynucleotides, polypeptides or carbohydrates.

Preferably, the polymers are synthetic polymers. Examples of synthetic polymers include polyvinyl alcohol, polyethylene glycerol, PVP, polyolefins, fluoropolymers, hydropolymers from vinyl esters, vinyl ethers, carboxy vinyl monomers, meth(acrylic) acid, acrylamide, N-vinyl pyrrolidone, acylamidopropanem acylamidopropane, PLURONIC (Maleic acid, NN-dimethylacrylamide diacetone acrylamide acryloyl, morpholine and mixtures thereof. Biodegradable polymers such as oxidized regenerated cellulose or polylactide/polyglycolide copolymers may also be used.

Alternatively, natural polymers such as carbohydrates (e.g. dextran, chitin or chitosan) natural peptides or proteins (collagens, gelatins, elastin, fibronectins, or even soluble proteins such as albumin), or semi synthetic peptides (made by using a peptide synthesizer or by recombinant techniques) may be used.

In a preferred embodiment, polymers of N-(2-hydroxypropyl) methylacrylamide (HPMA) are used. In this regard, reference is made to Ulbrich et al. (1980) *Biomaterials* 1, 199-204, which details the crosslinking of HPMA polymers by peptides.

As mentioned above, the polymers are joined by cross-linkages which comprise cleavable oligopeptidic sequences. Oligopeptides are generally defined as polypeptides of short length, typically twenty amino acids or fewer. Preferably, the oligopeptidic sequences employed in the present invention consist of 3 to 15 amino acids, preferably 3 to 10 amino acids, more preferably, 3 to 8 amino acids and yet more preferably 4 to 8 amino acids. Preferably, the oligopeptidic sequences consist of 3, 4, 5, 6, 7 or 8 amino acids.

The degree of crosslinking of the polymers should be sufficient such that the rate of release of the therapeutic agent increases in the presence of the protease. Preferably, the degree of crosslinking of the polymers should be sufficient to render the matrix sufficiently impermeable to the molecule to be delivered so that the therapeutic agent is only released in the presence of the target protease. This will be dependent on the molecular weight of the therapeutic agent.

The rate of degradation of the matrix will depend on a number of factors, including the length of the oligopeptidic sequences. Ulbrich et al. noted that extension of the peptidic linkers by one amino acid residue to give a peptidic linker of four amino acids caused a pronounced rise in the rate of cleavage of the polymeric substrates. Ulbrich et al. reported that extension of the oligopeptidic sequence led to a decrease in the steric hindrance by polymer chain and thus to an increase in degradability.

Steric hindrance may also be reduced by coupling the oligopeptidic sequence to the polymer by means of an appropriate spacer. Thus, the oligopeptidic sequences may couple the polymers directly (in which case the cross-linkage consists of the oligopeptidic sequence) or by means of an appropriate spacer.

The following paper gives a useful review of bioconjugation techniques for use in pharmaceutical chemistry: Veronese, F. M. and Morpurgo, M (1999) Bioconjugation in Pharmaceutical chemistry 11 Farmaco, 54, 497-516. This paper describes in detail the chemistry of each amino acid and which ones are most suitable for use in bioconjugation techniques. For example, it demonstrates that conjugation would occur by nucleophile to electrophile attacks. The amino acid side chains R—S—, R—$NH_2$, R—COO— and ═R—O— are well suited to bioconjugation (to natural or synthetic molecules).

In addition this paper indicates and gives examples of a wide range of structures and chemical groups that the peptides (containing amino (e.g. lysine), carboxyl (COO—) or cystyl groups (R—SH) can bind to.

With regard to conjugation techniques, see also Ulbrich, K., et al (2000) Polymeric drugs based on conjugates of synthetic and natural marcomolecules I. Synthesis and physico-chemical characterisation. Journal of controlled release 64, 63-79. This reference describes how antibodies, peptides or proteins can be conjugated to synthetic polymers (e.g. poly HPMA).

The rate of degradation will not only depend on the number of amino acids but also on the nature of the amino acids comprising the cross-links. This dependency arises from the substrate specific nature of proteases. The region of the enzyme where interaction with the substrate takes place is known as the "active site" of the enzyme. The active site performs the dual role of binding the substrate while catalysing the reaction, for example cleavage. Studies of the structures of the complexes of proteolytic enzymes with peptides indicate that the active site of these enzymes is relatively large and binds to several amino acid residues in the peptide. Thus, the degradability of a particular bond in a peptide chain depends not only on the nature of the structure near the cleaved bond, but also on the nature of the amino acid residues which are relatively remote from the cleaved bond, but play an important part in holding the enzyme in position during hydrolysis.

The structure of the oligopeptidic sequences must be chosen so as to correspond to that of the active site of the kaliikrein. Suitable peptide sequences include -Phe-Arg-Ser-Ser-Arg-GIn- (SEQ ID NO: 1) or -Met-Ile-Ser-Leu-Met-Lys-Arg-Pro-Gln- (SEQ ID NO: 2) that can be degraded by kallikrein at Lys-Arg or Arg-Ser bonds.

Preferably, the oligopeptidic sequences are cleavable only by a kallikrein. Alternatively, the oligopeptidic sequences may be cleavable by two, three or more proteases associated with wound fluid.

The design of the linking oligopeptidic sequence is important as it must not only contain a hydrolysable sequence that would be cleaved in the presence of the protease but also a terminal amino acid that can be readily conjugated to the polymers employed or to a spacer. Examples of reactive amino acids that could be used to link the oligopeptidic sequences to the polymers or spacers include cysteine and lysine.

The therapeutic agent may, for example, be an antimicrobial agent and/or a pain relieving agent. The antimicrobial agent may, for example, comprise an antiseptic, an antibiotic, or mixtures thereof. The pain relieving agent may comprise an anaesthetic, an analgesic, or a kallikrein inhibitor. Suitable anaesthetics include lidocaine or novocaine. Suitable analgesics include non-steroidal anti-inflammatory drugs (NSAIDs). Suitable kallikrein inhibitors include aprotonin, kallistatin, nafamostat mesilate, protease inhibitor-6 (as described in U.S. Pat. No. 6,472,143), and mixtures thereof. A particular advantage of including the kallikrein inhibitor as one of the active agents is that it can also be used to regulate the rate of breakdown of the polymer matrix by kallikrein. For example, the kallikrein inhibitor may be dispersed in the matrix at a level just sufficient to prevent breakdown of the matrix when the level of kallikreins in the ambient wound fluid is at non-painful levels, but not so high as to prevent breakdown of the matrix when the concentration of kallikreins exceeds a threshold characteristic of pain sensation. In other embodiments, the kallikrein inhibitors are encapsulated by the matrix material but not dispersed in the matrix material, so they do not interfere with the breakdown of the matrix material by the kallikreins.

In selecting one or more therapeutic agents for use with the wound dressings of the present invention, it is preferred that larger molecules are employed (e.g. molecules having a molecular weight of at least 500, 1,000, 5,000, 10,000, or 20,000). Small molecules may penetrate the matrix, whereas larger molecules such as chlorohexidine may be better suited to this type of application. Further, if a polyfunctional polymer is used the pore size of the matrix will be smaller and thus the ability of the matrix to retain the therapeutic agent in the absence of protease will be higher. Moreover, as noted above, the degree of cross-linking will influence the permeability of the matrix.

Preferred antibiotics include peptide antimicrobials (e.g. defensins, Magainin, synthetic derivatives of them) tetracycline, penicillins, terramycins, erythromycin, bacitracin, neomycin, polymycin B, mupirocin, clindamycin and mixtures thereof. Preferred antiseptics include silver sulfadiazine, chlorhexidine, povidone iodine, triclosan, other silver salts, sucralfate, quaternary ammonium salts and mixtures thereof.

The therapeutic agent may be incorporated within the matrix of the invention or may alternatively be located behind the matrix in a "donor layer". Thus, in one embodiment of the first aspect invention, the therapeutic agent is incorporated within the matrix. For ready release of the therapeutic agent upon elevation of the wound kallikrein level, the therapeutic agent should not be covalently bound to the matrix. For example, if the molecule to be delivered is relatively inert it could be mixed into the formulation during manufacture. Silver is one example of a molecule that could be delivered in this way. The wound contacting layer of the dressing may comprise or consist of the matrix into which the therapeutic agent has been incorporated. Alternatively, the dressing may comprise a liquid permeable wound contacting layer, an intermediate layer (which may be an absorbent layer) comprising or consisting of the matrix within which the therapeutic agent has been incorporated, and preferably also an outer, liquid-impervious backing layer. Upon degradation of the matrix by kallikrein present in wound fluid, the therapeutic agent present in the intermediate layer may diffuse into the wound.

Another embodiment of the first aspect of the invention provides a wound dressing which comprises a barrier layer which comprises the cross-linked matrix of the invention, the barrier layer being for initially separating the therapeutic agent in the wound dressing from wound fluid when in use. Suitably, the barrier layer consists of the matrix.

The barrier layer is separate from the therapeutic agent, and the therapeutic agent is initially prevented from contacting the wound fluid by the barrier layer. That is to say, the bioavailability of the therapeutic agent to the wound surface is low until the peptide cross-linkages in the barrier material have been broken down by the kallikrein enzyme, at which point the bioavailability of the therapeutic agent increases. Since kallikrein protease levels are elevated in painful wounds, such as some chronic and infected wounds, this provides for accelerated and/or selective release of the therapeutic agent into such wounds. The barrier layer is normally substantially impervious to wound fluid and insoluble therein unless the wound fluid contains a sufficient level of kallikrein to break down the substrate material.

The barrier layer is preferably about 0.1 to about 3 mm thick. Preferably about 0.5 to 1.5 mm thick. The cross-linked polymers may be combined in a film-forming composition with polymeric materials, plasticisers, and humectants. Suitable polymers include alginates, guar gum, carboxymethyl cellulose, methyl cellulose, hydroxypropyl methyl cellulose, locust bean gum, carrageenan, chitosan, heparan sulfate, dermatan sulfate, glycosaminoglycans such as hyaluronic acid, proteoglycans, and mixtures thereof. Suitable plasticisers include C2-C8 polyhydric alcohols such as glycerol. Preferably the cross-linked polymers make up at least about 10% by weight, more preferably at least about 20%, 30%, 40%, 50%, 60%, 70%, 80% or 90% by weight of the film-forming composition.

In certain embodiments the barrier layer comprises a substantially continuous film comprising the film forming composition of the cross-linked polymers as described above.

In other embodiments the barrier layer comprises an apertured sheet having a composition comprising the cross-linked polymers applied thereto in occlusive fashion. The occlusive composition may be similar to the film-forming composition described above. In these embodiments, the apertures typically make up from about 0.1% to about 50% of the area of the wound facing surface of the sheet before swelling, more typically from about 1% to about 30% of the area of the apertured sheet, and preferably from about 10% to about 25% of the area of the apertured sheet. Typically, the apertured sheet has from about 1 to about 30 apertures per square cm, for example from about 4 to about 15 apertures per square cm or from about 5 to about 10 apertures per square cm. In certain embodiments the apertures are uniformly distributed over the surface of the sheet, preferably in a regular pattern. The mean area of each aperture may for example be from about 0.01 to about 10 $mm^2$, preferably from about 0.1 to about 4 $mm^2$, and more preferably from about 1 $mm^2$ to about 2 $mm^2$. It will be appreciated that the sheet may include more than one size and shape of aperture in order to provide apertures that open more or less quickly on exposure to painful wound fluid. This enables still more control over the dynamics of therapeutic agent delivery to the wound. Typically, substantially the whole area of the apertures in the apertured sheet is blocked by the barrier material before exposure to wound exudate.

Preferably, the thickness of the barrier film or the apertured sheet (by ASTM D374-79) is from about 0.2 to about 5 mm, more preferably from about 0.4 to about 3 mm.

In one embodiment the barrier layer material may comprise, in addition to the cross-linked matrix of the invention, a polymer selected from the group consisting of water soluble macromolecular materials (hydrogels) such as sodium alginate, sodium hyaluronate, alginate derivatives such as the propylene glycol alginate described in EP-A-0613692, and soluble hydropolymers formed from vinyl alcohols, vinyl esters, vinyl ethers and carboxy vinyl monomers, meth(acrylic) acid, acrylamide, N-vinyl pyrrolidone, acylamidopropane sulphonic acid, PLURONIC (Registered Trade Mark) (block polyethylene glycol, block polypropylene glycol) polystyrene-, maleic acid, NN-dimethylacrylamide diacetone acrylamide, acryloyl morpholine, and mixtures thereof. Suitable hydrogels are also described in U.S. Pat. No. 5,352,508.

In one embodiment the barrier layer material may comprise, in addition to the cross-linked matrix of the invention, a polymer selected from the group consisting of bioerodible polymers such as polylactidelpolyglycolide, collagen, gelatin, polyacrylate gels such as those described in EP-A-0676457, calcium alginate gels, cross-linked hyaluronate gels, gels of alginate derivatives such as propylene glycol alginate, and gels wherein the hydropolymer is formed from vinyl alcohols, vinyl esters, vinyl ethers and carboxy vinyl monomers, meth(acrylic) acid, acrylamide, N-vinyl pyrrolidone, acylamidopropane sulphonic acid, PLURONIC (Registered Trade Mark) (block polyethylene glycol, block polypropylene glycol) polystyrene-, maleic acid, NN-dimethylacrylamide diacetone acrylamide, acryloyl morpholine, and mixtures thereof. Suitable hydrogels are also described in U.S. Pat. No. 5,352,508.

The barrier layer material may further comprise from about 5 to about 50% by weight, preferably from 15 to 40% by weight, on the same basis of one or more humectants such as glycerol. The barrier layer material may further contain up to about 30% w/w, more preferably up to about 15% w/w on the same basis of water.

The matrix of the invention comprising the therapeutic agent may contact the barrier layer directly, or may be separated therefrom for example by an absorbent layer.

Preferably, the wound dressing of the invention comprises an absorbent layer and/or a backing layer. As will be evident from the above, the absorbent layer may, for example, separate the barrier layer from the therapeutic agent containing cross-linked matrix or alternatively the absorbent layer may comprise the therapeutic agent containing cross-linked matrix.

The area of the optional absorbent layer is typically in the range of from 1 $cm^2$ to 200 $cm^2$, more preferably from 4 $cm^2$ to 100 $cm^2$.

The optional absorbent layer may comprise any of the materials conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. The basis weight of the absorbent layer may be in the range of 50-500 $g/m^2$, such as 100-400 $g/m^2$. The uncompressed thickness of the absorbent layer may be in the range of from 0.5 mm to 10 mm, such as 1 mm to 4 mm. The free (uncompressed) liquid absorbency measured for physiological saline may be in the range of 5 to 30 g/g at 25°.

Preferably, the wound dressing further comprises a backing layer covering the barrier sheet and the optional absorbent layer on the side opposite the wound-facing side of the dressing. The backing layer preferably provides a barrier to passage of microorganisms through the dressing and further preferably blocks the escape of wound fluid from the dressing. The backing layer may extend beyond at least one edge of the barrier sheet (if present) and optional absorbent layer to provide an adhesive-coated margin adjacent to the said edge for adhering the dressing to a surface, such as to the skin of a patient adjacent to the wound being treated. An adhesive-coated margin may extend around all sides of the barrier sheet (if present) and optional absorbent layer, so that the dressing is a so-called island dressing. However, it is not necessary for there to be any adhesive-coated margin.

Preferably, the backing layer is substantially liquid-impermeable. The backing sheet is preferably semipermeable. That is to say, the backing sheet is preferably permeable to water vapour, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 $g/m^2$/24 hrs, preferably 500 to 2000 $g/m^2$/24 hrs at 37.5° C. at 100% to 10% relative humidity difference. The backing sheet thickness is preferably in the range of 10 to 1000 micrometers, more preferably 100 to 500 micrometers.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive layer (where present) should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 $g/m^2$, and more preferably 50 to 150 $g/m^2$. Polyurethane-based pressure sensitive adhesives are preferred.

Preferably, the adhesive layer extends outwardly from the absorbent layer and the envelope to form an adhesive-coated margin on the backing sheet around the absorbent layer as in a conventional island dressing.

Also within the scope of the present invention are embodiments in which the cross-linked matrix material substantially encapsulates the therapeutic agent. For example, the dressing may comprise, or consist essentially of, particles such as microspheres of therapeutic agent (e.g. antimicrobial material or kallikrein inhibitor) encapsulated in a layer comprising the cross-linked matrix material. The particles are preferably loaded with from 1 to 90 wt. %, more preferably from 3 to 50 wt. % of the therapeutic agent.

The particles may be made by any suitable technique, including comminution, coacervation, or two-phase systems for example as described in U.S. Pat. No. 3,886,084. Techniques for the preparation of medicated microspheres for drug delivery are reviewed, for example, in *Polymeric Nanoparticles and Microspheres*, Guiot and Couvreur eds., CRC Press (1986).

A preferred method for preparation of the microparticles is coacervation, which is especially suited to the formation of particles in the preferred size range of 100 to 500 micrometers having a high loading of therapeutic agents. Coacervation is the term applied to the ability of a number of aqueous solutions of colloids, to separate into two liquid layers, one rich in colloid solute and the other poor in colloid solute. Factors which influence this liquid-liquid phase separation are: (a) the colloid concentration, (b) the solvent of the system, (c) the temperature, (d) the addition of another polyelectrolyte, and (e) the addition of a simple electrolyte to the solution. Coacervation can be of two general types. The first is called “simple” or “salt” coacervation where liquid phase separation occurs by the addition of a simple electrolyte to a colloidal solution. The second is termed “complex” coacervation where phase separation occurs by the addition of a second colloidal species to a first colloidal solution, the particles of the two dispersed colloids being oppositely charged. Generally, materials capable of exhibiting an electric charge in solution (i.e. materials which possess an ionizable group) are coacervable. Such materials include natural and synthetic macromolecular species such as gelatin, acacia, tragacanth, styrene-maleic anhydride copolymers, methyl vinyl ether-maleic anhydride copolymers, polymethacrylic acid, and the like.

If, prior to the initiation of coacervation, a water-immiscible material, such as an oil, is dispersed as minute droplets in an aqueous solution or sol or an encapsulating colloidal material, and then, a simple electrolyte, such as sodium sulfate, or another, oppositely charged colloidal species is added to induce coacervation, the encapsulating colloidal material forms around each oil droplet, thus investing each of said droplets in a liquid coating of the coacervated colloid. The liquid coatings which surround the oil droplets must thereafter be hardened by cross-linking to produce solid-walled microcapsules Preferably, the wound dressing according to any aspect of the present invention is sterile and packaged in a microorganism-impermeable container.

The invention claimed is:

1. A wound dressing comprising a therapeutic agent and a matrix comprising polymers joined by cross-linkages which cross-linkages comprise oligopeptidic sequences which are cleavable by a kallikrein such that the rate of release of the therapeutic agent increases in the presence of the kallikrein, wherein the oligopeptide sequence comprises -Phe-Arg-Ser-Ser-Arg-Gln- (SEQ ID NO: 1) or -Met-Ile-Ser-Leu-Met-Lys-Arg-Pro-Gln- (SEQ ID NO: 2), wherein the polymer is a polymer of N-(2-hydroxypropyl) methyacrylamide (HPMA) and wherein the therapeutic agent is an antimicrobial agent, a pain relieving agent, an antiseptic, an analgesic, a local anaesthetic, or a kallikrein inhibitor.

2. A wound dressing according to claim 1, wherein the therapeutic agent is incorporated within the matrix.

3. A wound dressing according to claim 2, wherein the dressing further comprises a wound contacting layer wherein the wound contacting layer comprises the matrix within which the therapeutic agent is incorporated.

4. A wound dressing according to claim 2, wherein the dressing comprises a liquid permeable wound contacting layer, an intermediate layer comprising the matrix within which the therapeutic agent is incorporated and an outer, liquid-impervious backing layer.

5. A wound dressing according to claim 1, wherein the dressing comprises a barrier layer which comprises the matrix, the barrier layer being for initially separating the therapeutic agent in the wound dressing from wound fluid when in use.

6. A wound dressing according to claim 5, wherein the barrier layer comprises an apertured sheet having a composition comprising the cross-linked polymers applied thereto in occlusive fashion.

7. A wound dressing according to claim 5, wherein a layer of the therapeutic substance is provided behind the barrier layer.

8. A wound dressing according to claim 7, wherein an absorbent layer is provided behind the barrier layer and the therapeutic substance is dispersed in the absorbent layer.

9. A wound dressing according to claim 8, wherein the barrier layer substantially encapsulates the therapeutic substance.

10. A wound dressing according to claim 4, wherein the wound dressing comprises an absorbent layer and/or a backing layer.

* * * * *